United States Patent [19]
Conviser et al.

[11] Patent Number: 5,874,113
[45] Date of Patent: Feb. 23, 1999

[54] SHELF LIFE IMPROVEMENT FOR ETHYLENE OXIDE STERILANT MIXES

[75] Inventors: Stephen Alan Conviser, Morristown, N.J.; Arthur Edward Holmer, Lewiston, N.Y.

[73] Assignee: AlliedSignal Inc., Morristown, N.J.

[21] Appl. No.: 543,745

[22] Filed: Oct. 16, 1995

[51] Int. Cl.⁶ .......................... A61K 33/00; A61K 31/02
[52] U.S. Cl. ........................ 424/700; 514/743; 514/747; 514/757
[58] Field of Search .............................. 424/700; 514/743, 514/747, 757

[56] References Cited

U.S. PATENT DOCUMENTS

| | | | |
|---|---|---|---|
| 3,068,064 | 12/1962 | McDonald | 21/58 |
| 3,372,980 | 3/1968 | Satas | 21/58 |
| 5,039,485 | 8/1991 | Conviser et al. | 422/34 |
| 5,342,579 | 8/1994 | Conviser et al. | 514/475 |
| 5,376,333 | 12/1994 | Shanklant et al. | 422/34 |

FOREIGN PATENT DOCUMENTS

| | | |
|---|---|---|
| 0 125 520 A2 | 11/1984 | European Pat. Off. . |
| WO 90/03807 | 4/1990 | European Pat. Off. . |
| 0 385 798 A1 | 9/1990 | European Pat. Off. . |
| WO 91/01764 | 2/1991 | European Pat. Off. . |
| 0 566 892 A2 | 10/1993 | European Pat. Off. . |
| WO 93/23086 | 11/1993 | European Pat. Off. . |
| WO 94/06481 | 3/1994 | European Pat. Off. . |

OTHER PUBLICATIONS

Conviser, Stephen A., "Hospital Sterilization Using Ethylene Oxide—What's Next?" *Journal of Healthcare Materiel Management*, Jul. 1989 (Reprint).
0 566 892 A2 English Abstract.

*Primary Examiner*—Zohreh Fay
*Attorney, Agent, or Firm*—Jay P. Friedenson; Colleen D. Szuch

[57] ABSTRACT

A method of increasing the shelf life of a sterilant mixture of ethylene oxide and one or more halocarbons when the mixture is in contact with iron oxide on the surface of a storage vessel. Sufficient carbon dioxide is added to the mixture to reduce the reactivity of the iron oxide for converting ethylene oxide to reaction products of ethylene oxide. In an alternate embodiment, a hollow carbon steel vessel which holds a mixture of ethylene oxide and a halocarbon as a sterilizing gas has its inside surface passivated by forming a reaction product of iron oxide and carbon dioxide.

20 Claims, No Drawings

SHELF LIFE IMPROVEMENT FOR ETHYLENE OXIDE STERILANT MIXES

BACKGROUND OF THE INVENTION

1. Field of the Invention

The present invention relates to the field of sterilizing gases and more particularly to sterilization based on the use of ethylene oxide.

2. Description of the Prior Art

It is known in the art to sterilize articles by the application of boiling water or steam to the article to be sterilized. However, in the field of medicine among others, there is a need to employ sterilant compositions because many articles cannot withstand the temperature or moisture associated with steam sterilization. Sterilization with a germicidal agent, such as ethylene oxide gas or ethylene oxide containing gas mixtures has played an important role in sterilizing heat or moisture sensitive materials. Ethylene oxide is a widely used sterilant since it is both an inherently effective sterilant and its residues rapidly volatize from the article to be sterilized. Although ethylene oxide alone may be used to carry out sterilization, this is not done because ethylene oxide is a highly flammable gas. Ethylene oxide forms explosive mixtures in air from about 3.0 volume percent to 100 volume percent ethylene oxide. Thus, when ethylene oxide is used alone as a sterilizing gas, precautions such as explosion proof equipment are necessary. Therefore, ethylene oxide sterilant is generally used in a mixture with a flame retardant. Gaseous sterilization of reuseable medical and surgical equipment using a nonflammable mixture of ethylene oxide and a carrier gas has proven to be reliable, cost effective technology for many hospitals. The flame retardant component, must complement the properties of the ethylene oxide or the beneficial effects of the ethylene oxide will be lost. Inert carrier gases inhibit the flammability of ethylene oxide and provide sufficient autogeneous vapor pressure to deliver the liquid mixture from the source cylinder to the heat exchanger of the sterilizer vessel where the liquid mixture is vaporized. The most typical flame retardant chosen for use with ethylene oxide in a sterilant mixture has been dichlorodifluoromethane which known in the industry as CFC-12. The most commonly used sterilant mixture is a mixture of 12 weight percent ethylene oxide and 88 weight percent CFC-12. This mixture is commonly referred to in the industry as 12–88. In recent years CFC-12 has become undesirable since it is a chlorofluorocarbon which is believed to cause significant damage to the ozone layer in the upper atmosphere. Accordingly, worldwide reduction and elimination of the use of CFC-12 is now underway. This has created a problem for the use of ethylene oxide as a sterilant. Another flame retardant which is known for use with ethylene oxide is carbon dioxide. However a nonflammable ethylene oxide/carbon dioxide mixture contains less than 40 percent of the ethylene oxide per unit volume as does 12–88. Thus, sterilization must be carried out either at higher pressures or for longer contact times. Furthermore the large difference in the vapor pressures of ethylene oxide and carbon dioxide causes the mixture to separate as it is being withdrawn from the storage tank or cylinder, raising the danger of delivering a sterilant mixture rich in carbon dioxide, which will not sterilize, or rich in ethylene oxide, which is explosive.

As a result, improved sterilant mixtures employing ethylene oxide and other flame retardant halocarbons have been developed. These are exemplified in U.S. Pat. Nos. 5,342,579; 5,376,333 and 5,039,485 which are incorporated herein by reference. Although the major purpose of the inert carrier gas component in these sterilizing gas mixtures is to mask the flammability characteristics of ethylene oxide, simple substitution of an arbitrary nonflammable gas does not necessarily ensure a useful sterilizing gas mixture.

Almost universally, sterilant mixtures employing ethylene oxide and a flame retardant halocarbon are produced in manufacturing facilities whose piping and other vessels comprises carbon steel. In addition, the sterilant mixture is stored, transported and used in refillable pressurized cylinders comprising carbon steel. Unfortunately carbon steel eventually degrades to iron oxide. It has been found that this iron oxide, in both its alpha and gamma forms, assists in the degradation of ethylene oxide to reaction products of ethylene oxide such as acetaldehyde, ethylene glycol, polyethylene glycol and other reaction products. These reaction products form oils, contaminate the sterilant mixture, stain medical devices, clog lines and tubing and render the sterilant mixture unusable. Shelf life of the mixture is only a few months at best. It has now been unexpectedly found that when the surface of the vessels in contact with the sterilant mixture has been treated by exposure to carbon dioxide, the shelf life is extended. There is a substantial decrease in the production of ethylene oxide reaction products and the sterilant mixture has a substantially extended shelflife. In another embodiment of the invention, carbon dioxide gas is intimately admixed with the ethylene oxide and hydrohalocarbon. The carbon dioxide contained in this latter mixture achieves the iron oxide passivation in the vessel, avoids subsequent fouling, yet the overall mixture retains its favorable sterilizing, non-explosive and flame retardancy properties. This result using ethylene oxide, halocarbon and carbon dioxide is surprising since, the use of carbon dioxide in sterilant atmospheres had been shown to be a polymerization promoter. Tests have demonstrated polymer growth rates from ethylene oxides to be ten to twenty times faster in the presence of carbon dioxide than CFC-12. See Conviser, Stephen A., "Hospital Sterilization Using Ethylene Oxide—What's Next?", Journal of Healthcare Materiel Management, July 1989.

It would therefore be desirable to provide an improved ethylene oxide/hydrohalocarbon sterilant mixture which has a substantially reduced production of unwanted reaction products of ethylene oxide. Additionally, sterilization is carried out with the composition of this invention at acceptable pressures and contact times and without unacceptable mixture separation upon withdrawal from the storage cylinder.

SUMMARY OF THE INVENTION

The invention provides a method of reducing the conversion of ethylene oxide to reaction products of ethylene oxide when such ethylene oxide is present in a mixture with one or more halocarbons and the mixture is disposed in contact with a surface of an iron oxide containing vessel. The method comprises contacting the iron oxide containing surface of the vessel with a sufficient amount of carbon dioxide under conditions sufficient to reduce its reactivity for converting ethylene oxide to reaction products of ethylene oxide. The iron oxide containing surface of the vessel may be contacted with the carbon dioxide either prior to or during contacting the surface with the mixture of ethylene oxide and one or more halocarbons.

The invention also provides a composition which comprises an intimate admixture of ethylene oxide, one or more halocarbons and carbon dioxide.

The invention further provides an article which comprises a hollow carbon steel vessel capable of receiving, holding and dispensing a gas, which vessel has an inside surface comprising the reaction product of iron oxide and carbon dioxide. A mixture is contained in the vessel, which mixture comprises ethylene oxide and one or more halocarbons. The mixture may further comprises carbon dioxide.

DETAILED DESCRIPTION OF THE PREFERRED EMBODIMENT

One embodiment of the invention provides a sterilant comprising an admixture of ethylene oxide, one or more halocarbons and carbon dioxide. The halocarbon may be a single halocarbon or a mixture of halocarbons. Preferably the halocarbon is a hydrohalocarbon such as a hydrofluorocarbon or hydrochlorofluorocarbon and more preferably a monochlorotetrafluoroethane, pentafluoroethane or dichlorotrifluoroethane. Suitable halocarbons non-exclusively include 1,1-dichloro-2,2,2-trifluoroethane (HCFC-123), 1,1,2,2,2-pentafluoroethane (HFC-125), 1,1,2,2-tetrafluoroethane (HFC-134), 1,2,2,2-tetrafluoroethane (HFC-134a), 1-chloro-1,2,2,2-tetrafluoroethane (HCFC-124), 1-chloro-1,1,2,2-tetrafluoroethane (HCFC-124a), chlorodifluoromethane (HCFC-22), dichlorodifluoromethane (CFC-12), trichlorofluoromethane (CFC-11), tetrafluoromethane (HFC-14), trifluoromethane (HFC-23), heptafluoropropane (HFC-227) and hexafluoropropane (HFC-236).

When the composition of the invention comprises each of ethylene oxide, one or more halocarbons and carbon dioxide, it comprises sufficient ethylene oxide to produce an effective sterilant composition. Such preferably comprises from about 6.3 to about 99 volume percent, or more preferably from about 14 to about 30 volume percent of ethylene oxide. The ethylene oxide acts as the active sterilizer while the halocarbon acts as a flame retardant. The composition comprises sufficient halocarbon to render the composition non-flammable. In order for a sterilant mixture to be non-flammable it must be non-flammable at all concentrations of air, i.e. from 0 to 100 percent air. The composition preferably comprises from about 1 to about 94 volume percent, or more preferably from about 70 to about 95 volume percent of halocarbon. At halocarbon concentrations less than the specified amount, sufficient flame retardancy may not be present in the mixture to avoid a potentially dangerous flammability situation, and at halocarbon concentrations greater than the specified amount, effective sterilization may not be possible without the use of undesirably high temperatures, pressures and/or contact times. The composition also comprises sufficient carbon dioxide to passivate iron oxide on the inside surface of the vessel contacting the mixture and reduce its reactance with ethylene oxide to produce reaction products of ethylene oxide. The composition preferably comprises from about 0.1 to about 30 volume percent, or more preferably from about 0.1 to about 10 volume percent of carbon dioxide. The carbon dioxide in the mixture has also been found to increase the vapor pressure of the overall mixture compared to a mixture without the carbon dioxide. In the preferred embodiment, the vapor pressure of the mixture is such that a pump is not required to remove the mixture from its storage vessel. Preferred vapor pressure of the mixture ranges from about 24 psia to about 615 psia, or more preferably from about 40 psia to about 350 psia, as measured at room temperatures, i.e. at about 70° F.

In an alternate embodiment of the invention, the inside surface of an iron oxide containing vessel is pre-passivated by contact with carbon dioxide prior to charging the vessel with the sterilant. The carbon dioxide is charged into the vessel in a sufficient amount and for a sufficient reaction time to passivate the catalyst (iron oxide) and prevent converting ethylene oxide to reaction products of ethylene oxide. These amounts may be easily determined by those skilled in the art. Useful amounts of carbon dioxide for this purpose may be that amount which achieves an internal vessel pressure ranging from about 0.1 atmospheres to about 10 atmospheres, however this range is not critical and may vary by allowing more or less contact time for passivation. A useful reaction time may range from about 1 hour to about 48 hours, depending on the amount of carbon dioxide present.

The sterilant may then either comprise a mixture of only the ethylene oxide and hydrohalocarbon as is known in the art, for example from the above enumerated U.S. patents, or the above described intimate admixture of ethylene oxide, halocarbon and carbon dioxide. The sterilant mixture of this invention may be used to sterilize medical equipment such as diagnostic endoscopes; plastic goods such as syringes; test tubes; incubators; pacemakers; rubber goods such as tubing, gloves, catheters and sheeting; instruments such as needles and scalpels; and other items such as dilators, pumps and intraocular lenses. In addition, the sterilant mixture of this invention may be used as a fumigant for items outside the medical field. These items include certain foodstuffs such as spices; furs, bedding, paper goods, and transportation equipment such as the cargo area of airplanes, trains and ships.

The sterilant mixture of this invention is effective against unwanted insects, bacteria, virus, molds, fungi, and other microorganisms. The sterilant mixture of this invention may be prepared using any effective mixing technique well known to those skilled in the art. For example, each compound of the mixture may be pumped gravimetrically through a manifold into a sterilant container, and the container rolled to intermix the compounds into a homogeneous mixture. Alternatively, the compounds may be pumped into a mixing tank, recirculated in the tank until a fully homogeneous mixture is formed, and then pumped from the mixing tank into a sterilant container. The sterilant mixture of this invention may be packaged in storage containers of suitable design such as those meeting U.S. Dept. of Transportation (DOT) Specification 4BA 240, 4BA 300, 4BW 240 or other DOT specification cylinders or trailers of suitable working pressure. The sterilant mixture may also be packaged in American Society of Mechanical Engineers (ASME) suitable storage vessels. The storage cylinder may be delivered to the use site holding the sterilant mixture at a pressure generally within the range of from about 70 to 190 psia at 70° C. F., and connected through a series of valves, control valves, vaporizer and appropriate conduit to a sterilizer to carry out the sterilization.

The basic gaseous sterilization process consists of evacuating the sterilization chamber containing articles to be sterilized, preconditioning the articles at an optimal relative humidity, admitting the sterilizing gas at an appropriate pressure and temperature, maintaining contact between the sterilizing atmosphere and the articles to be sterilized for an appropriate time, and finally discharging and evacuating the chamber to remove the sterilant gas. The sterilant mixture of this invention may be used with any commonly employed sterilizer known to the art. Although there are many variations on the basic process, the major factors which have to be controlled in order to effect the sterilization are exposure time, temperature, ethylene oxide pressure or partial pressure, and relative humidity. A description of the standard sterilization processes and apparatus with which the gaseous sterilizing agents of the invention are useful may be found in J. J. Perkins Principles and Methods of Sterilization, at 501–530 (2d ed. 1969); and Ethylene Oxide Gaseous Sterilization For Industrial Applications, Industrial Sterilization International Symposium, 181–208 (1972); U.S. Pat. Nos. 3,068,064 and 3,589,861.

Sterilizing chambers may range in size from desk-top to room-size models and even larger. After the items are placed within sterilization chamber the chamber is heated generally to a temperature within the range of from 1000° F. to 1400° F. Generally the higher the temperature the shorter is the required exposure time. After the chamber is brought up to operating temperature, a partial vacuum is drawn inside the chamber by pumping out air. The air removal serves both to prevent dilution of the sterilant mixture and to reduce the exposure pressure. Since a moist microorganism is more susceptible to the action of the sterilant, water vapor is preferably employed to create a relative humidity within the chamber in the range of from about 20 to about 80 percent.

The pressure at which the sterilization takes place within the chamber may be from about 20 to 40 psia. The sterilization time varies depending on a number of factors including temperature, concentration, humidity level, the specific sterilant mixture employed, the chamber loading, the bioburden, the sterility assurance level desired and the material being sterilized. For example, porous articles require shorter exposure time to achieve sterility than articles sealed in polyethylene bags. Moreover, some bacteria are especially resistant and thus take longer to destroy. Following the required exposure time, the sterilant mixture is evacuated from the chamber by flushing with air, nitrogen, steam or carbon dioxide. The sterilized material is then removed from the chamber and, if necessary, aerated for the removal of residual sterilant, before being used.

The following non-limiting example serves to illustrate the invention.

EXAMPLE 1

Oxyfume 2000 is a mixture of 8.6 weight percent ethylene oxide and the balance HCFC-124 which is commercially available from AlliedSignal Inc. of Morristown, New Jersey. Oxyfume 12 is a mixture of 12.0 weight percent ethylene oxide and the balance CFC-12 which is also commercially available from AlliedSignal Inc. of Morristown, New Jersey. This example demonstrates lowering the non-volatile residue (NVR) growth rate in Oxyfume 2000 and to increase the vapor pressure as much as possible without altering the product significantly.

A set of previously used F cylinders is given a 100 milliliter flush with pure HCFC-124 to remove any residual NVR. A normal fill density of Oxyfume 2000 of 115 percent and a nominal water fill weight of an empty F cylinder of 2890 grams allows a maximum of 3324 grams of mixture in each container. A fill weight of 3000 grams of mixture is chosen for convenience of calculation and on scale filling. A series of cylinders is connected to a laboratory fill rack, evacuated and placed in an ice bath on a 30 kilogram capacity balance. The cylinders are tared to zero and 258.5, 257.7 and 258.0 grams of ethylene oxide vapor is condensed into cylinders numbered F-9982, F-1531 and F-634235E respectively. The cylinders are then brought up to 3000.9, 3000.3 and 3000.5 grams total weight respectively by transferring liquid phase HCFC-124 into each container. Condensed ethylene oxide vapor is used in all cases to minimize any contaminant carryover from the source cylinder. The ethylene oxide weight percentages for the cylinders are 8.61, 8.59 and 8.59 respectively. Each cylinder is rotated for 15 minutes to ensure complete mixing. Immediately after mixing, 0.45 weight percent (1.15 mole percent) carbon dioxide is added to cylinders F-9982 and F-1531 to determine if the NVR growth could be slowed down or prevented. F-1531 is chosen for carbon dioxide addition because it previously showed significant polymer growth. F-9982 is also chosen for carbon dioxide addition. The cylinders are again mechanically rolled to ensure complete mixing. After the cylinders returned to room temperatures the vapor pressure is measured by gauge to be approximately 31 psig. The first NVR test is run the following day.

Non Volatile Residue Measurement

The following procedure is used to make the NVR determinations. Clean twelve 150 mL size glass beakers with detergent and dry the beakers in an oven at 105° C. Allow the beakers to cool in a desiccator for at least 30 minutes. Weigh the beakers on an analytical balance to the nearest 0.1 mg. Weigh the mixture cylinders and discharge approximately 100 grams each of liquid into three beakers from each cylinder. Allow the liquid to vaporize under a hood. The three unused beakers act as controls. Weigh the mixture cylinders again. After all liquid has vaporized, place the beakers in a 105° C. oven for 15 minutes. Allow the beakers to cool in a desiccator for at least 30 minutes. Weigh the beakers on an analytical balance to the nearest 0.1 mg. Calculate the number of milligrams of NVR per 100 grams of Oxyfume 2000 contained in the product discharged from the cylinders.

Results

A summary of the number of milligrams of NVR experimentally found per 100 grams of product is determined for the test cylinders as a function of days at 21 degrees Celsius and is given in Table II. Table I is a control testing of a similar composition without carbon dioxide for comparison purposes. In all cases the liquid samples observed in the beaker were clear, colorless and very mobile. The final NVR levels were 5.75±0.26, 11.39±0.57 and 31.16±0.66 milligrams per 100 grams of Oxyfume 2000 for cylinders F-9982 (with Carbon Dioxide), F-1531 (with Carbon Dioxide) and F-634235E (without Carbon Dioxide) respectively. The results obtained from the comparative round of tests without any carbon dioxide were 13.3±0.5, 45.1±1.8 and 20.4±0.1 milligrams per 100 grams of Oxyfume 2000 for cylinders F-9982, F-1531 and F-634235E respectively.

Results from the first test (no carbon dioxide—Table I) will be noted as (1) and the second test (with carbon dioxide—Table II) as (2). Cylinder F-634235E was actually used as a control for the two tests. Controls for tests (1) and (2) were conducted with only Oxyfume 2000. A comparison of results (1) and (2) for cylinder F-634235E show a very similar growth rate. This is noteworthy as the second test in a series generally shows a NVR growth reduction due to internal passivation from the first test. This is known as the flush and fill effect. There is no overall appearance of this effect in this series as the day 160 results are about the same.

The most dramatic results were obtained with F-1531. Test (1) showed a quickly accelerating growth rate that would make the product unusable. Test (2) is clearly under control with a much slower growth rate. Cylinder F-9982 test (1) results were the best of that series. In test (2) NVR is further reduced to even lower levels. An overall comparison of tests (2) and (1) for cylinders F-9982 and F-1531 show an approximately 50 percent NVR growth rate reduction. These are excellent results and make the Oxyfume 2000 rate comparable to the Oxyfume 12 rate. An additional benefit to this method is an approximately 12 percent increase in vapor pressure at room temperature. It is clear from these results that the addition of carbon dioxide to Oxyfume 2000 reduces the rate of NVR growth. By comparison, in the absence of carbon dioxide, the Oxyfume 2000 NVR growth rate is approximately two times the NVR growth rate of Oxyfume 12. The reduced rate compares favorably to the rate of NVR growth of Oxyfume 12.

TABLE I (Test 1-Comparative - All Cylinders Without Carbon Dioxide)

Experimental NVR Determinations Data Summary
(milligrams NVR per 100 grams Oxyfume 2000)

| Time Elapsed (days) | Cylinder F-9982 | Cylinder F-1531 | Cylinder F-634235E |
|---|---|---|---|
| 1 | 1.1 ± 0.2 | 0.6 ± 0.2 | 0.9 ± 0.1 |
| 34 | 2.5 ± 0.3 | 1.9 ± 1.4 | 1.4 ± 0.6 |
| 69 | 3.9 ± 0.1 | 14.1 ± 1.1 | 7.0 ± 1.4 |
| 99 | 8.9 ± 0.2 | 27.0 ± 0.4 | 11.6 ± 1.0 |
| 133 | 11.3 ± 0.8 | 36.2 ± 3.5 | 15.0 ± 0.6 |
| 162 | 13.3 ± 0.5 | 45.1 ± 1.8 | 20.4 ± 0.1 |

All samples were triple determinations with a blank correction. All cylinders stored at 21 degrees Celsius. Day 34 results were calculated without a blank correction.

TABLE II

Experimental NVR Determinations Data Summary
(milligrams NVR per 100 grams Oxyfume 2000)

| Time Elapsed (days) | Cylinder F-9982 (w/$CO_2$) | Cylinder F-1531 (w/$CO_2$) | Cylinder F-634235E (w/o $CO_2$) |
|---|---|---|---|
| 1 | 0.47 ± 0.17 | 0.64 ± 0.66 | 0.53 ± 0.30 |
| 32 | 1.01 ± 0.27 | 1.67 ± 0.46 | 1.97 ± 0.24 |
| 57 | 0.94 ± 0.19 | 1.74 ± 0.16 | 2.78 ± 0.08 |
| 86 | 1.69 ± 0.58 | 3.31 ± 0.45 | 5.83 ± 0.51 |
| 120 | 2.94 ± 0.64 | 5.79 ± 0.32 | 10.26 ± 0.38 |
| 149 | 2.92 ± 0.56 | 6.24 ± 0.12 | 16.42 ± 0.62 |
| 179 | 5.75 ± 0.26 | 11.39 ± 0.57 | 31.16 ± 0.66 |

All samples were triple determinations with a blank correction. All cylinders stored at 21 degrees Celsius.

EXAMPLE 2

This example demonstrates a pre-treatment (passivation) of the inside surface of a cylinder surface. A container such as a pressure cylinder, tank or truck is purged with nitrogen gas to remove residual air and moisture. Nitrogen purging is done to remove air and moisture to reduce flammability and contamination. Removal of moisture is important since water can hydrolyze ethylene oxide into ethylene glycol, the first step of polymerization. Nitrogen purging is carried out by filling the containers to two or three atmospheres with process nitrogen (99.5% or better purity). The nitrogen is then vented. The nitrogen fill is generally repeated two or three times. The containers are evacuated to a negative pressure of 27 inches of mercury. The containers are then filled to a pressure of two atmospheres with carbon dioxide. The are allowed to stand over night (sixteen hours) to passivate the inside surface of the container. Containers can then be treated in one of two ways. The carbon dioxide can be left in the container and a mixture of ethylene oxide and HCFC-124 can be directly filled into the container. Alternatively, the container is evacuated and filled with a mixture of carbon dioxide, ethylene oxide and HCFC-124.

The process for preparing a mixture of ethylene oxide and HCFC-124 typically involves the use of a 5000 (or more) pound mixing tank mounted on a scale platform. The ethylene oxide and HCFC-124 are added separately to this tank by pumping from source rail cars, tank storage or portable containers. The mixture is produced by weighing the appropriate amounts of ethylene oxide and HCFC-124. The batch is then mixed by a circulation pump. This mixed product is then pumped into previously evacuated containers. For a mixture of carbon dioxide, ethylene oxide and HCFC-124, this approach must be slightly modified to allow for the addition of the appropriate weight of carbon dioxide after the HCFC-124 is added to the mixing tank. Then normal circulation would mix up the product completely. The mixed product can then be transferred to evacuated cylinders or truck for distribution and use.

What is claimed is:

1. A method of increasing the shelf life of a mixture of ethylene oxide and one or more halocarbons when the mixture is in the presence of iron oxide which comprises adding carbon dioxide to the mixture in a sufficient amount to reduce the reactivity of the iron oxide for converting ethylene oxide to reaction products of ethylene oxide.

2. The method of claim 1 wherein the one or more halocarbons comprises one or more a hydrofluorocarbons or hydrochlorofluorocarbons.

3. The method of claim 1 wherein the one or more halocarbons comprises one or more components selected from the group consisting of monochlorotetrafluoroethanes, dichlorotrifluoroethanes, pentafluoroethanes, tetrafluoroethanes, heptafluoropentanes and hexafluoropropanes.

4. A method of reducing the conversion of ethylene oxide to reaction products of ethylene oxide when such ethylene oxide is present in a mixture with one or more halocarbons and the mixture is disposed in contact with a surface of an iron oxide containing vessel which method comprises contacting the iron oxide containing surface of the vessel with a sufficient amount of carbon dioxide under conditions sufficient to reduce its reactivity for converting ethylene oxide to reaction products of ethylene oxide.

5. The method of claim 4 wherein the iron oxide containing surface of the vessel is contacted with the carbon dioxide prior to contacting the surface with the mixture of ethylene oxide and one or more halocarbons.

6. The method of claim 4 wherein the iron oxide containing surface of the vessel is contacted with the carbon dioxide during contacting the surface with the mixture of ethylene oxide and one or more halocarbons.

7. The method of claim 4 wherein the iron oxide containing surface of the vessel is contacted with the carbon dioxide both prior to and during contacting the surface with the mixture of ethylene oxide and one or more halocarbons.

8. The method of claim 4 comprising adding carbon dioxide to the mixture.

9. The method of claim 4 wherein the one or more halocarbons comprises one or more hydrofluorocarbons or hydrochlorofluorocarbons.

10. The method of claim 4 wherein the one or more halocarbons comprises one or more components selected from the group consisting of monochlorotetrafluoroethanes and dichlorotrifluoroethanes.

11. A composition which comprises an intimate admixture of ethylene oxide, one or more halocarbons and carbon dioxide.

12. The composition of claim 11 which comprises from about 6.3 to about 99 volume percent of ethylene oxide; from about 1 to about 94 volume percent of one or more halocarbons; and from about 0.1 to about 30 volume percent of carbon dioxide.

13. The composition of claim 11 wherein the one or more halocarbons comprises one or more hydrofluorocarbons or hydrochlorofluorocarbons.

14. The composition of claim 11 wherein the one or more halocarbons comprises one or more components selected from the group consisting of monochlorotetrafluoroethanes, dichlorotrifluoroethanes, pentafluoroethanes, tetrafluoroethanes, heptafluoropentanes and hexafluoropropanes.

15. The composition of claim 11 wherein the one or more halocarbons comprises one or more components selected from the group consisting of 1,1-dichloro-2,2,2-trifluoroethane; 1,1,2,2,2-pentafluoroethane; 1,1,2,2-tetrafluoroethane; 1,2,2,2-tetrafluoroethane; 1-chloro-1,2,2,2-tetrafluoroethane; 1-chloro-1,1,2,2-tetrafluoroethane; chlorodifluoromethane; dichlorodifluoromethane; trichlorofluoromethane; heptafluoropentanes and hexafluoropropanes.

16. An article which comprises a hollow vessel capable of receiving, holding and dispensing a gas, said vessel having an inside surface comprising the reaction product of iron oxide and carbon dioxide; and a mixture disposed in the vessel, which mixture comprises ethylene oxide and one or more halocarbons.

17. The article of claim 14 wherein the mixture further comprises carbon dioxide.

18. The article of claim 14 wherein the one or more halocarbons comprises one or more hydrofluorocarbons or hydrochlorofluorocarbons.

19. The article of claim 14 wherein the one or more halocarbons comprises one or more components selected from the group consisting of monochlorotetrafluoroethanes, dichlorotrifluoroethanes, pentafluoroethanes, tetrafluoroethanes, heptafluoropentanes and hexafluoropropanes.

20. The article of claim 14 wherein the vessel comprises carbon steel.

* * * * *

UNITED STATES PATENT AND TRADEMARK OFFICE
CERTIFICATE OF CORRECTION

PATENT NO : 5,874,113
DATED : February 23, 1999
INVENTOR(S) : Conviser et al.

It is certified that error appears in the above-identified patent and that said Letters Patent is hereby corrected as shown below:

Column 5, line 12, delete "1000°F" and substitute therefor -- 100°F. --.

Column 5, line 12, "1400°F" and substitute therefor -- 140°F. --.

Signed and Sealed this

Seventh Day of March, 2000

Attest:

Q. TODD DICKINSON

Attesting Officer

Commissioner of Patents and Trademarks